United States Patent [19]

Pinkerton

[11] 4,387,236

[45] Jun. 7, 1983

[54] LIQUID PHASE OXIDATION

[75] Inventor: Robert B. Pinkerton, Newark, Del.

[73] Assignee: E. I. Du Pont de Nemours and Company, Wilmington, Del.

[21] Appl. No.: 354,195

[22] Filed: Mar. 3, 1982

[51] Int. Cl.³ .......................................... C07D 307/36
[52] U.S. Cl. .................................... 549/505; 549/509
[58] Field of Search ................................ 549/505, 509

[56] References Cited

U.S. PATENT DOCUMENTS 4,172,838 10/1979 Garnett et al. ...................... 549/505
4,257,960 3/1981 Peterson ............................. 549/509
4,268,421 5/1981 Garnett et al. ...................... 252/441

FOREIGN PATENT DOCUMENTS 1027655 4/1966 United Kingdom .

Primary Examiner—Richard Raymond

[57] ABSTRACT

A process of removing solids from an aqueous redox catalyst system which solids are formed in the production of furan compounds from butadiene or a butadiene derivative by heating at 180°–280° C. in the presence of sufficient cupric ion or oxygen to oxidize the solids. The redox catalyst system contains iodine ions, copper at an oxidation state between 1 and 2, a solubilizing agent for cuprous ion which is soluble in water and forms a water-soluble complex with cuprous ion and, at least 20 moles per liter of water the medium havine a pH of less than 2.

12 Claims, No Drawings

LIQUID PHASE OXIDATION

BACKGROUND

1. Field of the Invention

A recently developed process for the production of furan involves treating a starting material such as butadiene in the presence of oxygen with an aqueous catalyst system comprising iodine, preferably from an alkali metal iodide, copper having an average oxidation state between 1 and 2, a solubilizing agent for cuprous ion which is soluble in water and forms a water soluble complex with cuprous ion and at least 20 moles per liter of water, the system having a pH value of less than about 2. Such a process is disclosed in U.S. Pat. Nos. 4,172,838; 4,257,960 and 4,268,421. When operating this process a black, amorphous, intractable, insoluble material is produced as a by-product. The present invention relates to an in situ process for disposal of the above-described by-product by oxidation. Removal of the by-product solids by filtration can result in large copper losses and some iodine loss due mainly to occlusion of catalyst solution in the wet filter cake.

2. Prior Art

British No. 1,027,655 discloses a process of oxidizing organic products and especially aldehydes and ketones containing 1–6 carbon atoms at 50°–120° C.

SUMMARY OF THE INVENTION

The present invention relates to an aqueous in situ oxidation of by-product solids by heating at 180° to 280° C. in the presence of oxygen or an oxidizing agent.

DETAILED DESCRIPTION

The present invention relates to a process of removing the solid impurities which form in a process of preparing furan. The process is for use in a process which uses as its starting material a compound of the formula

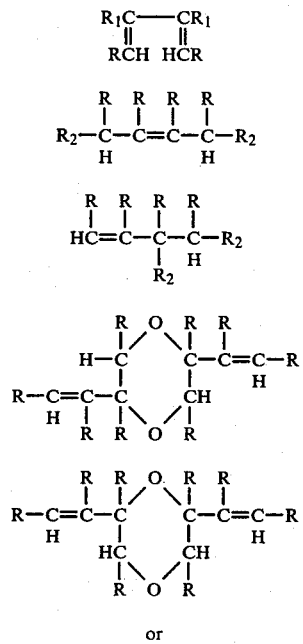

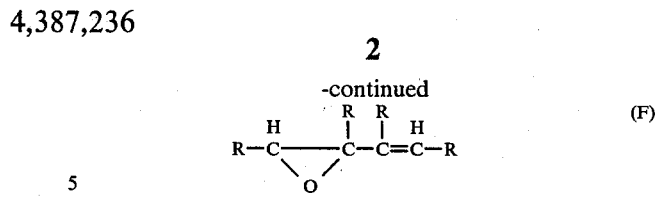

where R is hydrogen or an alkyl radical of 1–4 carbon atoms. Each $R_1$ is H, a halide or an alkyl group of 1–4 carbon atoms, with the proviso that the total number of carbon atoms in (A) does not exceed 8, $R_2$ is —OH, —$OR_1$ or

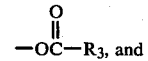

—$R_3$ is an alkyl radical of 1–4 carbon atoms, or (G) a mono or dihalo-substituted alkene of 4–8 carbon atoms.

The preferred starting materials are butadiene-1,3,2-butene-1,4-diol(cis and trans) and 1-butene-3,4-diol.

The catalyst system used is a redox system comprising water as the solvent, copper ions, and a solubilizing agent to keep the requisite number of $Cu^{+1}$ ions in solution.

It is preferred that water be used as the sole solvent or carrier for the system, but liquids in which water is diluted with up to 50%, by volume, of a hydrophilic solvent such as acetic acid, sulfolane, acetonitrile, dioxane or the like can also be used.

Preferably both $Cu^{+1}$ and $Cu^{+2}$ ions are present in the system, i.e., the copper preferably has an average oxidation state between 1 and 2, and most preferably between 1.3 and 1.90. As the process proceeds, the $Cu^{+2}$ ions are reduced to $Cu^{+1}$ ions, and the reaction slows or stops entirely until some of the $Cu^{+1}$ ions are oxidized back to $Cu^{+2}$ ions, as will be described later.

Copper ions are present in the system at a total concentration of about 0.1–10 moles per liter, preferably 0.5–3.5 moles per liter, and in $Cu^{+2}/Cu^{+1}$ mole ratios of 100/1 to ½, preferably 10/1 to ½.

The copper ions can be supplied by any water-soluble copper compound. Salts of the organic acids can be used; halides are preferred, and chlorides are expecially preferred. Salts of organic acids such as formic, acetic, propionic, trifluoroacetic, methanesulfonic, benzenesulfonic and p-toluenesulfonic can also be used. Mixtures of acids can also be used.

The solubilizing agent in the system can be any water-soluble inorganic or organic compound which forms a complex with $Cu^{+1}$ ions soluble enough in water to form a 0.2–3 molar solution. Illustrative of such agents are
alkali metal halides
alkaline earth metal halides
ammonium halides
iron halides
halogen acids
organic nitriles such as acetonitrile and succininitrile,
carboxylic acids such as acetic acid, thiocyanates such as
sodium thiocyanate, aliphatic amines such as tetramethylenediamine.

Solubilizing agents preferred for use are the alkali metal halides and the ammonium halides. Sodium chloride, potassium chloride, calcium chloride and ammonium chloride are especially preferred. Mixtures of solubilizing agents can also be used.

The solubilizing agent is present in the system at a concentration of about 0.01–5 moles per liter, preferably 0.3–5 moles per liter.

The redox system must be acidic. It is not possible to accurately express acidity of the system in terms of conventional pH values because the copper ions present interfere with pH measurements by the potentiometric method ordinarily used. Acidity of the system is therefore expressed in terms of hydrogen ion concentration, as measured by conventional titration techniques with standard base solutions, using such indicators as methyl red or methyl orange to determine end-point, as is well-known in the art.

The redox system should have a hydrogen ion concentration of 0.05–2 moles per liter, preferably 0.1–1 mole per liter. The hydrogen ions can be supplied by any acid which does not interfere with the reaction. Hydrochloric acid is preferred.

The process of the invention can be run intermittently or continuously. In the intermittent operation, a reaction vessel, made of material capable of withstanding the possible corrosive effects of the copper salts used, is charged with the redox system, which also functions as the reaction medium. The redox system is prepared by simply dissolving suitable amounts of copper salts, solubilizing agent and acid in an appropriate amount of water.

The solution is then brought to and held at a temperature of 80°–150° C., preferably 90°–105° C., with stirring, while the starting material is slowly fed in until the reaction slows or stops due to the lack of $Cu^{+2}$ ions.

Simultaneously with the starting material feed, the reaction mass is swept with an inert gas, preferably by bubbling it through. This agitates the mass, and the gas stream carries the furan compound out of the reactor as it is formed.

The gas used can be any that is inert to the reaction. Nitrogen, helium, water vapor and carbon dioxide are illustrative; nitrogen is preferred. The gas is fed into the reactor at a rate that will maintain about atmospheric pressure.

The furan compound product can be separated from the gas stream by any convenient technique, and is most easily done by condensation with conventional equipment. The gas can then be recycled if desired.

When the reaction has slowed or stopped, it is necessary to replenish the redox system with $Cu^{+2}$ ions. This is done by passing oxygen through the system. The oxygen can be introduced as molecular oxygen, or as a mixture of oxygen with other gases. For example, air can be used, or oxygen can be mixed with the inert gas used. The replenishment can be done in situ or can be carried out in a separate reactor. Oxygenation is continued until oxidation of the $Cu^{+1}$ ions to $Cu^{+2}$ ions has brought the $Cu^{+2}/Cu^{+1}$ ratio to the original level, as determined potentiometrically. The process can then be begun anew.

In continuous operation, the process is also begun by charging the reactor with the redox system. This is then brought to and held at 80°–150° C., preferably 90°–105° C., and stirred while starting material is fed in the rate of 0.0025–0.015 mole per liter per minute.

At the same time, a mixture of oxygen and inert gas, preferably nitrogen, in an oxygen/nitrogen weight ratio of 10–50/90–50, is fed into the reaction mass, again preferably by bubbling it through. This simultaneously removes furan product from the mass as it forms and replenishes the redox system. The gas mixture is fed into the mass at a rate predetermined to maintain the original $Cu^{+2}/Cu^{+1}$ ratio, as measured potentiometrically.

Furan compound product is continuously removed from the gas stream, preferably by condensation. The gas can be recycled if desired.

During the operation of the above-identified process, insoluble solids accumulate after several hours of operation. This is a black, amorphous; intractable material and the amount formed depends on a number of variables. The amount generally ranges from 2 to 10% of the starting material consumed. The yield loss is largely accounted for by this by-product and a small amount of carbon dioxide.

In a commercial scale plant large quantities of by-product solids would be generated. While the solids can be physically separated from the system and either landfilled or incinerated such a process would be cumbersome and expensive. The solids generally are a mixture of polymerized starting material species along with some non-polymeric oxidation and chlorination products.

It has now been found that these solids can be removed by a liquid phase, in situ oxidation. I have found that the solids are oxidized when the catalyst is heated to the 180° to 280° C. range. At lower temperatures, such as 130° C., the solids oxidation is much less complete and large quantities of heavy foam are produced. The solids can be oxidized by either cupric ion alone or by direct reaction with oxygen. Generally the solids are oxidized by the cupric ion and enough oxygen is added to regenerate the desired amount of cupric ion from cuprous ion. Generally the solids level in the redox catalyst system is allowed to reach the 0.1 to 1.0% by weight level when their removal by the process of the present invention takes place. Higher levels of solids in the redox catalyst system require levels of oxygen or air addition which are difficult to control on a continuous basis, and also cause problems with pluggage, pumping and foaming.

The products of the solids oxidation comprise approximately 96% by weight carbon dioxide and the remainder small quantities of many chlorinated and oxidized species. Between 97 and 100% of the solids are oxidized by holding the catalyst slurry at 180°–280° C. for 15 to 30 minutes and adding air or oxygen to regenerate cupric ion.

The temperatures used in the process of the present invention in conjunction with the corrosive catalyst, limits the reactor material of construction to glass lined reactors or tantalum or something as resistant to corrosion.

The catalyst solutions after the in situ solids oxidation of the present invention have not shown any decline in activity for the butadiene to furan reaction.

EXAMPLES

A glass-lined reactor containing 30 gallons (0.11 m$^3$) of a redox catalyst containing 1.6 moles per liter cuprous chloride, 1.2 moles per liter cupric chloride, 2.4 moles per liter potassium chloride, 0.05 mole per liter potassium iodide, 1.0 mole per liter hydrogen chloride and the remainder water is maintained at 100° C. Butadiene is fed to the reactor at a rate of approximately 1000 ml/min and furan is removed from the reactor as it is produced with a nitrogen purge. A large sample of the solids produced (1.3% by weight, of the reaction medium) is isolated from the above described reactor by filtration at 70°–80° C. The following is an elemental analysis of the solids. Run "A" is solids which have been given a minimum hot water wash and air dried. Run "B" is solids which were reslurried at 100° C. in 3 M potassium chloride, filtered, washed four times with hot water and air dried at 50° C. The percentages reported in Table I are by weight.

TABLE I

| Run | C % | H % | O % | I % | Cu % | Cl % |
|-----|-----|-----|-----|-----|------|------|
| A | 17 | 2.7 | 21 | 0.5 | 18.7 | 26.6 |
| B | 47 | 4.3 | 31 | 0.9 | 8.8 | 3.6 |

While some occlusion appears to be taking place, some of the chlorine and copper compounds appear to be chemically bound.

A series of Examples are performed illustrating the present invention. In each of Examples 1–5 a 380 ml platinium bomb is charged with 200 ml of an aqueous catalyst containing 0.24 moles of cupric ion and 0.32 moles of cuprous ion (Except Example 6 which used 200 cc water) and the number of grams of solids reported in Table II.

The bomb is pressured with oxygen at 1000 psig ($6.89 \times 10^6$ Pa) to add 0.5 mole of the system which contained an oxygen equivalent of 0.16 mole of oxygen in the solids. At the 16 g solids level used in Example 3, there is 0.62 mole of carbon present so that the total available $O_2$ and carbon oxidized is close to a 1:1 molar ratio. Each Example was run at 200° C. (Except Example 5 which was run at 250° C.) for 30 minutes plus and additional 20 minutes at greater than 150° C. for the heat up and cool down cycle.

TABLE II

| Example | Solids (g) start | Solids (g) end | Solids Oxidized % | Molar Cu+ start | Molar Cu+ end | pH start | pH end |
|---------|------|-----|-----|------|------|-----|-------|
| 1 | 12 | 0 | 100 | 0.32 | 0.09 | 1.0 | 0.005 |
| 2 | 15 | 0 | 100 | 0.32 | 0.09 | 1.0 | 0.17 |
| 3 | 16 | 0.67 | 98 | 0.32 | 0.33 | 0.3 | 0.47 |
| 4 | 18 | 3.9 | 78 | 0.32 | 0.3 | 1.0 | 0.92 |
| 5 | 18 | 0 | 100 | 0.32 | | 1.0 | 1.48 |
| 6 | 10 | 0 | 100 | 0 | 0 | 1.0 | 0.9 |

In Examples 1 and 2 the copper became over oxidized as indicated by the much lower Cu+ present at the end than at the start.

EXAMPLE 7

This Example illustrates oxidation of the solids using cupric ion only as the oxidizing agent, and shows that three moles of cupric ion can oxidize one mole of carbon in this system. A glass reactor is charged with 250 ml of a catalyst solution containing 0.5 mole Cu++ as cupric chloride, 0.6 mole potassium chloride, 0.012 mole KI, and 0.24 mole hydrochloric acid and 1.5 g of solids from Run B above. The reactor is sealed and heated to 280° C. for thirty minutes. The reactor is allowed to cool and then opened. Only a trace of solids remain and the catalyst solution contains 0.19 mole of Cu+ ion.

EXAMPLE 8

Sixteen grams of dry solids from Run B above are placed in a 380 ml platinum rocker bomb along with 200 ml (276 g) of the catalyst reported in Table III.

TABLE III

| | Start | End |
|---|-------|-----|
| CuCl | 0.32 mole | 0.27 mole |
| CuCl$_2$ | 0.24 mole | — |
| KCl | 2.4 mole | — |
| KI | 0.05 mole | — |
| HCl | 1.0 mole | 0.6 mole |
| mv at 100° C. | 400 mv | 400 mv |
| solids | 16 g | 0.82 g |
| Remainder water | | |

The bomb is pressured to 1000 psi ($6.9 \times 10^6$ Pa) with oxygen at room temperature.

The bomb is rocked and heated to 200° C. and held at that temperature for 20 minutes, after which the bomb is cooled, vented and discharged under nitrogen. The total weight of the material discharged is 273.1 g. The discharged material is a dark solution, typical of these catalyst solutions. The discharged material is heated and stirred at 92° C. under nitrogen. Samples are removed to analyze for acidity and percent CuCl, and the millivolt (mv) potential measured. The bulk of the discharged material is then filtered hot to isolate the unoxidized solids, which are then water washed and air dried to yield 0.82 g of solids (95% reduction of solids).

It has been demonstrated that regenerated catalyst system can be used to catalyze the production of furan from butadiene.

I claim:

1. A process of removing by-product solids formed in the preparation of furan compounds using an aqueous reaction medium comprising
   (a) elemental iodine or iodine from an alkali metal iodide,
   (b) copper having an average oxidation state greater than 1,
   (c) a solubilizing agent for cuprous ion which is soluble in water and forms a water-soluble complex with cuprous ion, and
   (d) at least 20 moles per liter of water, the medium having a pH value of less than about 2, wherein said aqueous reaction medium is heated at 180° to 280° C., while maintaining said aqueous reaction medium in the liquid phase, to oxidize at least 97 percent by weight of the solids present.

2. The process of claim 1 wherein oxygen is present.

3. The process of claim 2 wherein the heating is at from 200° C. to 280° C.

4. The process of claim 3 wherein the heating is done for from 15 to 30 minutes.

5. The process of claim 1 wherein the iodine is from an alkali metal iodide.

6. The process of claim 5 wherein the solubilizing agent is an alkali metal halide, an alkaline earth halide, or ammonium halide.

7. The process of claim 6 wherein the solubilizing agent is sodium chloride, calcium chloride or ammonium chloride.

8. The process of claim 7 wherein the copper is from cuprous chloride or cupric chloride.

9. The process of claim 7 wherein the copper is from cuprous bromide or cupric bromide.

10. The process of claim 8 wherein the iodine is from sodium iodide or potassium iodide.

11. The process of claim 10 wherein the furan was prepared from butadiene.

12. The process of claim 11 wherein the pH is less than 0.5.

* * * * *